(12) United States Patent
Murrell et al.

(10) Patent No.: US 8,936,814 B2
(45) Date of Patent: Jan. 20, 2015

(54) SKIN CREAM

(71) Applicants: Zuri A. Murrell, Long Beach, CA (US); Shalu Gupta-Murrell, Long Beach, CA (US)

(72) Inventors: Zuri A. Murrell, Long Beach, CA (US); Shalu Gupta-Murrell, Long Beach, CA (US)

( * ) Notice: Subject to any disclaimer, the term of this patent is extended or adjusted under 35 U.S.C. 154(b) by 0 days.

(21) Appl. No.: 13/690,595

(22) Filed: Nov. 30, 2012

(65) Prior Publication Data
US 2014/0154338 A1 Jun. 5, 2014

(51) Int. Cl.
| | | |
|---|---|---|
| A61K 33/30 | (2006.01) | |
| A61K 31/4164 | (2006.01) | |
| A61K 31/167 | (2006.01) | |
| A61K 31/573 | (2006.01) | |

(52) U.S. Cl.
CPC ........... *A61K 31/573* (2013.01); *A61K 31/4164* (2013.01); *A61K 31/167* (2013.01); *A61K 33/30* (2013.01)
USPC ....................................................... 424/642

(58) Field of Classification Search
None
See application file for complete search history.

(56) References Cited

U.S. PATENT DOCUMENTS

| | | | |
|---|---|---|---|
| 5,543,148 A | | 8/1996 | Lapidus |
| 5,719,197 A * | | 2/1998 | Kanios et al. ............... 514/772.6 |
| 5,773,023 A * | | 6/1998 | Deckner et al. .............. 424/449 |
| 5,948,416 A * | | 9/1999 | Wagner et al. ................ 424/401 |
| 6,004,566 A * | | 12/1999 | Friedman et al. ............. 424/400 |
| 6,322,820 B1 | | 11/2001 | Simoneau |
| 6,656,928 B1 | | 12/2003 | McCadden |
| 7,241,456 B2 * | | 7/2007 | Vromen ........................ 424/449 |
| 7,700,076 B2 * | | 4/2010 | Tamarkin et al. ............... 424/47 |
| 2002/0119174 A1 * | | 8/2002 | Gardlik et al. ................. 424/401 |
| 2002/0192273 A1 * | | 12/2002 | Buseman et al. .............. 424/449 |
| 2003/0059450 A1 * | | 3/2003 | Maibach et al. ............... 424/401 |
| 2003/0099678 A1 * | | 5/2003 | Maibach et al. ............... 424/401 |
| 2003/0194446 A1 | | 10/2003 | Akes et al. |
| 2003/0232091 A1 * | | 12/2003 | Shefer et al. ................... 424/490 |
| 2004/0127861 A1 | | 7/2004 | Glassman et al. |
| 2004/0138179 A1 | | 7/2004 | Goldstein et al. |
| 2005/0054991 A1 * | | 3/2005 | Tobyn et al. ................... 604/290 |
| 2006/0110415 A1 * | | 5/2006 | Gupta ............................ 424/401 |
| 2006/0193789 A1 * | | 8/2006 | Tamarkin et al. ............... 424/47 |
| 2006/0194759 A1 | | 8/2006 | Eidelson |
| 2007/0071711 A1 * | | 3/2007 | Vromen ........................ 424/74 |
| 2007/0196323 A1 * | | 8/2007 | Zhang et al. ............... 424/78.02 |
| 2007/0269393 A1 * | | 11/2007 | Wepfer .......................... 424/59 |
| 2008/0152894 A1 * | | 6/2008 | Beihoffer et al. ........... 428/317.9 |
| 2008/0193393 A1 * | | 8/2008 | Dayan ............................ 424/59 |
| 2008/0253973 A1 * | | 10/2008 | Tamarkin et al. ............... 424/47 |
| 2009/0053290 A1 * | | 2/2009 | Sand et al. ..................... 424/449 |
| 2009/0196840 A1 | | 8/2009 | Lorenzo |
| 2011/0005943 A1 * | | 1/2011 | Beihoffer et al. ............. 206/205 |
| 2011/0110988 A1 * | | 5/2011 | Susak et al. ................... 424/401 |

\* cited by examiner

*Primary Examiner* — Robert A Wax
*Assistant Examiner* — Olga V Tcherkasskaya
(74) *Attorney, Agent, or Firm* — Manali V. Dighe; Loza & Loza, LLP

(57) ABSTRACT

A topical composition is provided. The topical composition comprises from about 0.25 to about 1.5 percent by weight hydrocortisone; from about 0.5 to about 5.0 percent by weight lidocaine; and from about 0.25 to about 3.0 percent by weight clotrimazole.

10 Claims, No Drawings

SKIN CREAM

BACKGROUND OF INVENTION

Many times, for example, an infant may develop a diaper rash. Often times, a variety of different creams and/or compositions are needed to treat the rash, i.e., anti-fungal cream, barrier cream, moisturizer, and the like. Many times one or more of the foregoing do not work. Accordingly, a cream and/or a composition is needed that may treat/reduce the rash, i.e., a single cream and/or composition.

SUMMARY OF PREFERRED EMBODIMENTS

In a preferred embodiment, a topical composition is provided. The composition includes from about 0.25 to about 1.5 percent by weight hydrocortisone; from about 0.5 to about 5 percent by weight lidocaine; and from about 0.25 to about 3 percent by weight clotrimazole. In one aspect of that embodiment, the topical composition is in the form of a lotion or cream. The topical composition may comprise from about 70 to about 99 percent by weight water. The topical composition may comprise from about 1 to about 7 percent by weight zinc oxide. The topical composition may comprise an aloe vera extract. The topical composition may comprise a rose oil extract.

In a preferred embodiment, a topical composition consisting essentially of water; hydrocortisone; lidocaine; clotrimazole; zinc oxide; emollient; and an herb is provided. Preferably, the emollient is aloe vera extract. Preferably, the herb is rose oil.

In a preferred embodiment, a topical composition consisting essentially of water; hydrocortisone; lidocaine; clotrimazole; and zinc oxide is provided. Preferably, the percent by weight of water is greater than about 50% by weight.

In a preferred embodiment, a topical composition consisting essentially of water; hydrocortisone; lidocaine; clotrimazole; zinc oxide; and emollient is provided.

In a preferred embodiment, a method of relieving skin discomfort is provided. The method includes the step of providing a topical composition comprising: from about 0.25 to about 1.5 percent by weight hydrocortisone; from about 0.5 to about 5.0 percent by weight lidocaine; and from about 0.25 to about 3 percent by weight clotrimazole. The method further includes the step of applying the topical composition to an affected area of the skin from about 1 to about 5 times a day. Preferably, the skin discomfort is anal discomfort. In one aspect, the anal discomfort is caused by hemorrhoids.

In a preferred embodiment, a topical composition is provided. The topical composition includes one or more anti-inflammatory agents; one or more topical anesthetics; one or more anti-fungal agents; and less than 5% by weight alcohol. The topical composition may further comprise greater than 50% by weight water. The topical composition may further comprise less than 2% by weight alcohol. The topical composition may further comprise greater than about 70% by weight water. In one aspect, the topical composition may comprise greater than 75% by weight water.

DETAILED DESCRIPTION OF THE INVENTION

The present invention relates to a composition that preferably comprises an anti-inflammatory steroid, a topical anesthetic, an anti-fungal agent, and zinc oxide. Preferably, this composition is topically applied to treat skin discomfort, particularly anal discomfort. As such, preferably, the composition of the present invention is topical. The anal discomfort may be caused by, but not limited to, one or more of the following: hemorrhoids and/or anal fissures. An anal fissure is a tiny tear in the external skin of the anus, which despite its small size may be extremely painful. Anal fissures often are caused by passage of very hard stool and/or irritation due to diarrhea. A hemorrhoid may begin when a vein in the anus or rectum becomes painfully engorged with blood and swollen. Hemorrhoids may be caused by constipation and/or straining to pass a bowel movement. Other causes of anal discomfort that may be treated with the composition of the present invention include, but are not limited to: rectal polyps; anal abscess; anal hematoma; pinworm infestation; and/or cancer. In other embodiments, the composition of the present invention may be used to treat skin discomfort on any other body part/location, and its use is not limited to treat skin discomfort at or near the anus.

As used herein, "anal discomfort" may refer to "anal skin discomfort." As used herein, "skin discomfort" may refer to skin pain, inflammation, soreness, redness, itching, swelling, irritation, dryness, fungus, and the like. For example, the composition of the present invention may be used to treat skin pain and inflammation (i.e., diaper rash). It is to be understood that the use of the composition is not limited to treating skin discomfort.

In a preferred embodiment, the composition of the present invention may be used to treat a variety of diseases and/or conditions that cause skin discomfort, including, but not limited to: hemorrhoids and fissures; psoriasis; eczema; dermatitis; rashes and/or irritation caused by insect bites, soaps, detergents, cosmetics, jewelry; and the like.

In a preferred embodiment, the composition of the present invention may be used to treat diaper rash. A diaper rash is a skin problem that develops in the area beneath an infant's and/or toddler's diaper. It may be caused by infection with a yeast and/or fungus called *Candida*. In other embodiments, the composition of the present invention may not be used to treat diaper rash.

As used herein, "plurality" means "one or more."

In a preferred embodiment, the composition comprises one or more anti-inflammatory agents and/or one or more topical corticosteroids; or a plurality of topical corticosteroids. Topical corticosteroids may share anti-inflammatory, antipruritic, and/or vasoconstrictive actions. More preferably, the anti-inflammatory agent is hydrocortisone. Hydrocortisone is the main glucocorticoid secreted by the adrenal cortex. Its synthetic counterpart may be used in the treatment of various skin conditions. Preferably, the hydrocortisone is the active ingredient in the composition. Hydrocortisone may be known as, but is not limited to, the following names: cortisol; 4-Pregnene-11beta, 17alpha, 21-triol-3,20-dione; 11beta,17alpha, 21-Trihydroxypregn-4-ene-3,20-dione; Kendall's compound F; Reichstein's substance M; 17-hydroxycorticosterone; C21H30O5; 50-23-7; cortef; cetacort; dermacort; cobadex; hycort; signef; and/or optef. Preferably, the hydrocortisone used in the present invention is available from Medisca and/or Paddoea. Preferably, it is available in a powder form. In other embodiments, in lieu of, or in addition to hydrocortisone, one or more of the following may be used: alcometasone; dexamethasone; hydrocortisone 21-acetate; hydrocortisone 17-valerate; hydrocortisone 17-butyrate; dexamethasone 21-phosphate; chloroprednisone acetate; cortodoxone; meprednisone; betamethasone 17-valerate; bethamethasone 17,21-dipropionate; descinolone acetonide; bethamethasone valerate; prednisolone; fluorometholone; flucloronide; cortisone acetate; amicinafal; flunisolide acctate; triamcinolone acetonide; flucinonide; desconide; hydrocortisone; betamethasone; cyclopentylpropionate; and the like; and mixtures thereof; and equivalents thereof. It is to be understood that any anti-inflammatory agent and/or topical corticosteroid may be used in the composition of the present invention. In other embodiments, the anti-inflammatory agent/topical corticosteroid is omitted.

In a preferred embodiment, the composition comprises one or more topical anesthetics (or a plurality of topical anesthetics). Preferably, the topical anesthetic is lidocaine. In other embodiments, in lieu of, or in addition to, lidocaine, one or mare of the following may be used: benzocaine, butamben, dibucaine, oxybuprocaine, pramoxine, proparacaine, proxymetacaine, tetracaine, amethocaine, propoxycaine, mepivacaine, bupivacaine, and the like, and mixtures thereof and equivalents thereof. Preferably, the topical anesthetic is available from, but not limited to, Medisca, Paddoea, or the like. Preferably, lidocaine is available in the powder form. In yet other embodiments, the topical anesthetic is omitted.

In a preferred embodiment, the composition comprises one or more anti-fungal agents for a plurality of anti-fungal agents). Preferably, the anti-fungal agent is clotrimazole. Clotrimazole is an imidazole derivative with a broad spectrum of antimycotic activity. It may inhibit biosynthesis of the sterol ergostol, an important component of fungal cell membranes. Its action leads to increased membrane permeability and apparent disruption of enzyme systems bound to the membrane. In other embodiments, in lieu of, or in addition to, clotrimazole, one or more of the following may be used: 1-[(2-chlorophenyl)-diphenylmethyl]imidazole; fluconazole; ketoconazole; itraconazole; lotrimin; canesten; mycosporin; mycelex; clotrimazol; mykosporin; empecid; gyne lotrimin; chlotrimazole, and the like, and mixtures thereof and equivalents thereof. Preferably, its chemical structure is $C_{22}H_{17}ClN_2$. Preferably, the anti-fungal agent is available from, but not limited to, Medisca and/or Paddoea, or the like. Preferably, it is available in a powder form. In yet other embodiments, the anti-fungal agent is omitted.

In a preferred embodiment, the composition comprises zinc oxide. It is generally a mild astringent and topical protectant with some antiseptic action. It may be used, for example, as a drying agent and/or as a sun-block. Preferably, it is in the form of an ointment and/or cream. Preferably, the zinc oxide is available from, but not limited to, Medisca, Paddoea, or the like. In other embodiments, in lieu of, or in addition to, zinc oxide, one or more of the following may be used: oxozinc; amalox; and the like. In other embodiments, the zinc oxide is omitted.

In a preferred embodiment, the composition comprises one or more emollients (or a plurality of emollients). Preferably, the emollient is a plant component, and/or a herbal component. As used herein, "emollient" may be interchangeable with "moisturizer." Emollients may be chemical agents specially designed to make the external layers of the skin (epidermis) softer and more pliable. Preferably, the emollient is aloe vera extract and rose oil (i.e., the essential oils extracted from various types of rose). Additionally, the emollient/herbal component may be arnica. Preferably, aloe vera extract and rose oil are available from Medisca and/or Paddoea, or the like. In lieu of, or in addition to, aloe vera extract and/or rose oil and/or arnica, the following may be used: chamomile extract; chamomile flower extract; cetearyl alcohol; isopropyl myristate; triglyceride; myristic acid; palmitic acid; PEG-60 hydrogenated castor oil; glceryl linoleate; cyclomethicone; dimethicone; decyl oleate; stearic acid; lanolin; plant oils; shea butter; cocoa butter; algae extract; aloe vera; althaea extract; angelica extract; arnica; avocado oil; borage seed oil; buckthorn; calendula; camellia oil; capsaicin; castor oil; chamomile oil; lemongrass extract; lime oil; marula oil; olive oil; panthenol; corn oil; flaxseed oil; gingseng extract; haxel oil; pomegranate seed oil; rice bran oil; shea butter, montana flower extract; essential oils; hawthrone herb; ginger; and the like, and mixtures thereof, and equivalents thereof. It is to be understood that the composition may comprise aloe vera extract (and not rose oil) or rose oil (and not the aloe vera extract) without departing from the scope of the present invention. In other embodiments, the emollient may not be a plant component or a herbal component, i.e., it may be a synthetically manufactured component. In yet other embodiments, the emollient is omitted (i.e., both the aloe vera extract and the chamomile extract are omitted).

In a preferred embodiment, the composition comprises one or more vitamins. For example, the following may be used: vitamin E; arnica; montana flower extract; any other plant extract; essential oils; hawthrone herb; ginger; beta-carotene; potassium; vitamin A; vitamin B complexes; vitamin $B_{12}$; vitamin C; and the like. In other embodiments, the vitamin may be omitted.

In a preferred embodiment, the composition of the present invention comprises one or more emulsifying agents and/or stabilization factors for a plurality of emulsifying agents and/or stabilization factors). As used herein, "emulsifying agent" may be interchangeable with "emulsifier" and "stabilizing agent." The emulsifying agent, for example, may be used to control the degree of viscosity of the composition and/or stabilize and/or solubilize the various components in the composition. The type of emulsifying agent used may depend on the degree of viscosity. Emulsifiers have different strengths or HLB ("hydrophilic lipophillic balance") values. Different emulsifiers are used depending on whether the composition is an O/W or a W/O composition. Preferably, the composition of the present invention is an O/W (oil-in-water) composition (however, a water-in-oil composition may be used. Examples of emulsifying agents include, but are not limited to, beeswax, surfactants, detergents, emulsifying wax, cetearyl alcohol, polysorbate 20, ceteareth 20, and the like, mixtures thereof, and/or equivalents thereof. In other embodiments, the emulsifying agent is omitted.

In a preferred embodiment, the composition of the present invention comprises one or more excipients and/or one or more pharmaceutically effective carriers. Preferably, the excipients/carriers are chosen so that they are generally compatible with the individual components of the present invention and do not interfere significantly with their transport through a person's skin. The excipients/carriers of the present invention may be in the form of a composition having more than one compound. Examples of excipients include, but are not limited to: glycerin; waxes; petroleum jelly, deionized water; water; mineral oil; salicylic acid; methylsulfonymethane (MSM); jojoba oil; fatty acid esters; alcohol; polyglycol; and the like, mixtures thereof; and equivalents thereof; and/or other organic compounds. In other embodiments, the excipient and/or pharmaceutically effective carrier is omitted.

In a preferred embodiment, the composition of the present invention may comprise one or more optional ingredients. These may include, but are not limited to, agents to adjust pH; coloring agents; buffers; neutralizing agents; coloring agents; decoloring agents; emulsion stabilizers; viscosity builders; humectants; preservatives; antioxidants; chemical stabilizers; and solvents. In other embodiments, the optional ingredients are omitted.

In a preferred embodiment, the composition comprises from about 0.25 to about 1.5 percent by weight hydrocortisone. More preferably, the composition comprises from about 0.50 to about 1.0 percent by weight hydrocortisone. Most preferably, the composition comprises from about 0.75 to about 1.0 percent by weight hydrocortisone. For example, the composition of the present invention may comprise about 1% by weight hydrocortisone. In other embodiments, the composition may comprise greater than about 1.5 percent by weight hydrocortisone or less than about 0.25 percent by weight hydrocortisone. In yet other embodiments, the maximum dosage of hydrocortisone allowed without prescription is used. It is to be understood that if a governmental agency such as the FDA (Federal Drug Administration) increases the maximum dosage of hydrocortisone allowed without prescription, that increased amount may be used in the composition of the present invention.

In a preferred embodiment, the composition comprises from about 0.5 to about 5.0 percent by weight lidocaine. More preferably, the composition comprises from about 1.0 to about 4.0 percent by weight lidocaine. Most preferably, the composition comprises from about 2 percent to about 4 percent by weight lidocaine. For example, the composition of the present invention may comprise about 2 percent by weight lidocaine. In other embodiments, the composition may comprise greater than about 5 percent by weight lidocaine or less than about 0.5 percent by weight lidocaine.

In a preferred embodiment, the composition comprises from about 0.25 to about 3 percent by weight clotrimazole. More preferably, the composition comprises from about 0.5 to about 2 percent by weight clotrimazole. Most preferably, the composition comprises from about 0.75 to about 1.5 percent by weight clotrimazole. For example, the composition of the present invention may comprise about 1% by weight clotrimazole. In other embodiments, the composition may comprise greater than about 3 percent by weight clotrimazole or less than about 0.25 percent by weight clotrimazole.

In a preferred embodiment, the composition comprises from about 1 to about 7 percent by weight zinc oxide. More preferably, the composition comprises from about 3 to about 6 percent by weight zinc oxide. Most preferably, the composition comprises from about 4 to about 5 percent by weight zinc oxide. For example, the composition of the present invention may comprise about 5% by weight zinc oxide. In other embodiments, the composition may comprise greater than about 7 percent by weight zinc oxide or less than about 1 percent by weight zinc oxide.

In a preferred embodiment, the composition comprises from about 0.25 to about 8 percent by weight aloe vera extract. More preferably, the composition comprises from about 2 to about 6 percent by weight aloe vera extract. Most preferably, the composition comprises from about 3 to about 5 percent by weight aloe vera extract. For example, the composition of the present invention may comprise about 4 percent by weight aloe vera extract. In other embodiments, the composition may comprise greater than about 4 percent by weight aloe vera extract or less than about 0.25 percent by weight aloe vera extract.

In a preferred embodiment, the composition comprises from about 0.10 to about 6 percent by weight rose oil. More preferably, the composition comprises from about 0.25 to about 4 percent by weight rose oil. Most preferably, the composition comprises from about 0.5 to about 3 percent by weight rose oil. For example, the composition of the present invention may comprise 1.5 percent by weight of rose oil. In other embodiments, the composition may comprise greater than about 6 percent by weight rose oil or less than about 0.10 percent by weight rose oil.

In a preferred embodiment, the composition of the present invention compromises from about 1 to about 10 percent arnica; more preferably from about 1.5 to about 8 percent arnica; most preferably from about 2 to abut 4 percent arnica. In other embodiments, the composition may comprise greater than about 4 percent by weight arnica or less than about 2 percent by weight arnica. In yet other embodiments, arnica may be omitted.

In a preferred embodiment, the composition of the present invention comprises from about 1 to about 4 percent by weight of emulsifying agent and/or wetting agent and/or surfactant. As used herein, "emulsifying agent" may be referred to "wetting agent" and/or "surfactant." More preferably, the composition comprises from about 1.5 to about 3 percent by weight emulsifying agent. Most preferably, the composition comprises from about 2 to about 2.5 percent by weight emulsifying agent and/or wetting agent. For example, the composition of the present invention may comprise 2 percent by weight of emulsifying agent. In other embodiments, the composition may comprise greater than 4 or less than 1 percent by weight emulsifying agent.

In a preferred embodiment, the composition of the present invention may be in the form of a cream. In other embodiments, the composition of the present invention may be in the form of a solution; spray; gel; lotion; ointment; liniment (balm); paste; film; suppository; and the like, and mixtures thereof, and equivalents thereof. It is to be understood that the ratio of water to base (i.e., oil) may be varied depending on the form of the composition desired and/or degree of viscosity desired. Lotions generally will require more water than for example, a cream. For example, creams may be semi-solid and may include an emulsion of water and oil in approximately equal forms. Preferably, the composition is available in such a form that it may be applied topically, i.e., on the surface of the skin and/or mucous membranes, transdermally, rectally, and/or vaginaly. In yet other embodiments, the composition may be in an ingestible form, i.e., a liquid or a tablet.

In a preferred embodiment, the degree of viscosity of the composition may be controlled by the use of suitable gelling and/or thickening agents. Preferably, the gelling and/or thickening agent is propylene glycol. In other embodiments, the gelling and/or thickening agent(s) may include, but are not limited to, oils; alcohols; fatty acids; various polymers; mixtures thereof; and equivalents thereof. Some examples of thickening and/or gelling agents include but are not limited to peanut oil; peppermint oil; rosemary oil; jojoba oil; sunflower oil; aluminum stearate; cetostearyl alcohol; propylene glycol; polyethylene glycol; polyacrylamide; hydroxypropyl cellulose; carboxyl vinyl polymers; C13-C14 isoparaffin; liquid paraffin; soft paraffin; laureth-7; woolfat; hydrogenated lanolin; beeswax; and mixtures thereof and equivalents thereof. In other embodiments, the degree of viscosity of the composition is not controlled by the use of suitable gelling and/or thickening agents.

In a preferred embodiment, the composition of the present invention may include a compounding base, i.e., a gel base. The gel base may be chosen, for example, based on the degree of viscosity desired. For example, the gel base may be water+ gelling agent. In this regard, the gelling agent may depend on the degree of viscosity desired. Examples of gel bases include, but are not limited to, KY jelly and/or Surgi-lube. This compounding base may be available from, but not limited to, pharmacy supply stores such as Paddock Labs; Perrigo; and/or Medisca.

In a preferred embodiment, the composition of the present invention is available over-the-counter. In this regard, the concentrations of the various ingredients are kept at a level that does not exceed the Federal Drug Administration requirements for an over-the-counter medication. It is to be understood however, that the composition of the present invention may be prescription strength. In this regard, for example, the hydrocortisone level may exceed about 1% by weight.

In a preferred embodiment, the composition of the present invention is formed by combining the ingredients identified herein. As used herein, "combining" may refer to mixing, compounding, and the like. Initially, the desired type of composition is identified. For example, a cream may be chosen as the appropriate form of the composition. In a preferred embodiment, the composition is made by combining clotrimazole powder, micronized hydrocortisone powder USP, lidocaine powder USP, and zinc oxide powder. Preferably, aloe vera freeze dried 200:1 powder is added to this combination. Preferably, an appropriate amount of gelling agent and/or propylene glycol liquid is added to the powder combination. Preferably, this powder/liquid combination is measured by liquid weight not volume. Preferably, compounding base (or "gel base") is added to the composition using geometric addition with mixing in between. Thereafter, the final desired weight is reached by adding compounding base ("gel base"). Preferably, the composition is then placed in an ointment mill (i.e., a Exakt three roll mill), and is run through the mill to produce a homogeneous mixture. Finally, the chamomile extract and/or rose oil are added. In other embodiments, one or more of the following is omitted and/or replaced by other suitable components: clotrimazole powder, micronized hydrocortisone powder USP, lidocaine powder USP; zinc oxide powder; and/or aloe vera freeze dried 200:1 powder. In yet other embodiments, the compounding base ("gel base") is omitted and/or replaced by another suitable component. In yet other embodiments, the composition is not placed in a ointment mill, and/or is placed in another suitable structure/device for ensuring a homogeneous mixture.

The following examples are presented to enable those skilled in the art to understand and practice the invention and to identify the presently preferred embodiments thereof. These examples are provided for illustrative purposes and not to indicate the scope of the invention, which is defined only by the appended claims.

EXAMPLE 1

An exemplary composition is made my mixing together the following:

Formulation #1

| Ingredients | % by weight |
| --- | --- |
| Water | 83% |
| Hydrocortisone | 1% |
| Lidocaine | 2% |
| Clotrimazole | 1% |
| Zinc oxide | 5% |
| Aloe vera extract | 4% |
| Rose oil | 2% |
| Wetting agent | 2% |

EXAMPLE 2

Formulation #2

| Ingredients | % by weight |
| --- | --- |
| Water | 84.5% |
| Hydrocortisone | 1% |
| Lidocaine | 2% |
| Clotrimazole | 1% |
| Zinc oxide | 5% |
| Aloe vera extract | 4% |
| Rose oil | 0.5% |
| Wetting agent | 2% |

EXAMPLE 3

Male patient has anal discomfort. He goes to the physician, and the physician indicates he has hemorrhoids. Male patient heads to his pharmacy and purchases an over-the-counter composition of the present invention. He applies the composition 3 times a day for 2 weeks, and notices a significant reduction in anal discomfort. For example, he may rub a dime-sized portion of the cream in the area of the discomfort.

EXAMPLE 4

Baby has redness and apparent discomfort in her diaper area. While her diaper is being changed, her parents apply the composition of the present invention to her diaper area. The composition is applied twice a day—once during the diaper change in the morning, and once during the diaper change in the evening. Within one day, baby's redness and apparent discomfort decreases.

EXAMPLE 5

The composition of the present invention may be prepared using the following steps:
(1) Calculate the amount of required of each ingredient (clotrimazole powder, micronized hydrocortisone powder USP, lidocaine powder USP, zinc oxide powder, and/or aloe vera freeze dried 200:1 powder) for the total amount to be prepared.
(2) Weigh each ingredient.
(3) Determine the appropriate amount of propylene glycol liquid to be added (liquid weight not volume).
(4) Add the appropriate amount of propylene glycol liquid to the combination/mixture/composition.
(5) Place the above contents on an ointment mill.
(6) Add chamomile extract and/or rose oil and/or arnica.

From the foregoing detailed description, will be evident that there are a number of changes, adaptations, and modifications, of the present invention, which come within the province of those skilled in the art. For example, the present invention includes all of the formulations disclosed herein. Further, the scope of the invention includes any combination of the elements from the different species, formulations, or embodiments disclosed herein, as well as subassemblies, assemblies, and methods of using and making thereof, and combinations of the various percentage ranges. It is intended that all such variations not departing from the spirit of the invention be considered as within the scope thereof.

What is claimed is:

1. A topical composition consisting of:
   (a) from about 0.25% to about 1.5% by weight of hydrocortisone;
   (b) from about 0.5% to about 5.0% by weight of lidocaine;
   (c) from about 0.25% to about 3.0% by weight of clotrimazole;
   (d) from about 70% to about 90% by weight of water;
   (e) from about 1% to about 6% by weight of zinc oxide;
   (f) from about 0.1% to about 8% by weight of one or more emollient plant components;
   (g) up to about 10% by weight of an emollient herb component;
   (h) from about 1% to about 4% by weight of one or more ingredients selected from the group consisting of wetting agents, emulsifying agents and surfactants;
   (i) one or more ingredients selected from the group consisting of excipients, pharmaceutically effective carriers, and compounding bases; and
   wherein the topical composition is in the form of a lotion or cream.

2. The topical composition of claim 1, wherein the topical composition comprises from about 3 to about 6 percent by weight zinc oxide.

3. The topical composition of claim 2, wherein the emollient plant component is aloe vera extract.

4. The topical composition of claim 2, wherein the emollient plant component is chamomile extract.

5. The topical composition of claim 2, wherein the emollient plant component is rose oil.

6. The topical composition of claim 2, wherein the emollient herb component is arnica.

7. The topical composition of claim 1, wherein the composition comprises:
   (a) about 1% by weight of hydrocortisone;
   (b) about 2% by weight of lidocaine;
   (c) about 1% by weight of clotrimazole;
   (d) greater than or equal to about 80% by weight of water;
   (e) about 5% by weight of zinc oxide;
   (f) about 4% by weight of aloe vera extract and about 0.5% to about 2% by weight of rose oil.

8. A method of relieving skin discomfort comprising:
   a. providing the topical composition of claim 1;
   b. applying the topical composition to an affected area of the skin.

9. The method of claim 8, wherein the skin discomfort is anal discomfort.

10. The method of claim 8, wherein the anal discomfort is hemorrhoids.

* * * * *